United States Patent
Lamberti et al.

(10) Patent No.: US 8,871,523 B1
(45) Date of Patent: Oct. 28, 2014

(54) WIRELESS SENSOR FOR DETECTING EXPLOSIVE MATERIAL

(71) Applicant: Babcock & Wilcox Technical Services Y-12, LLC, Oak Ridge, TN (US)

(72) Inventors: Vincent E. Lamberti, Oak Ridge, TN (US); Layton N. Howell, Jr., Knoxville, TN (US); David K. Mee, Knoxville, TN (US); Michael J. Sepaniak, Knoxville, TN (US)

(73) Assignee: Consolidated Nuclear Security, LLC, Reston, VA (US)

( * ) Notice: Subject to any disclaimer, the term of this patent is extended or adjusted under 35 U.S.C. 154(b) by 39 days.

(21) Appl. No.: 13/832,873

(22) Filed: Mar. 15, 2013

(51) Int. Cl.
*G01N 33/22* (2006.01)
*G01N 27/74* (2006.01)
*G01N 27/72* (2006.01)
*G01N 1/22* (2006.01)
*G01N 33/00* (2006.01)

(52) U.S. Cl.
CPC .................................. *G01N 33/0057* (2013.01)
USPC ............. 436/149; 436/84; 436/151; 436/181; 422/83; 422/88

(58) Field of Classification Search
CPC .......... G01N 33/0004; G01N 33/0057; G01N 33/20; G01N 33/203; G01N 33/22; G01N 33/227; G01N 1/22; G01N 1/2273; G01N 27/72; G01N 27/74; G01N 27/80
USPC ............. 436/73, 84, 149, 151, 181; 422/68.1, 422/69, 83, 88
See application file for complete search history.

(56) References Cited

U.S. PATENT DOCUMENTS

| | | | |
|---|---|---|---|
| 6,270,591 B2 | 8/2001 | Chiriac et al. | |
| 6,393,921 B1 | 5/2002 | Grimes et al. | |
| 7,694,346 B2 * | 4/2010 | Adams et al. | 850/7 |
| 7,824,619 B1 * | 11/2010 | Aviram | 422/88 |
| 2006/0032289 A1 * | 2/2006 | Pinnaduwage et al. | 73/25.05 |
| 2006/0231420 A1 * | 10/2006 | Garzon et al. | 205/775 |

OTHER PUBLICATIONS

M.D. Allendorf, et al.; "Stress-Induced Chemical Detection Using Flexible Metal-Organic Frameworks"; J. Am. Chem. Soc. 130 (2008) 14404.
Chiriac, et al; "Effect of Glass Removal on the Magnetic Behavior of FeSiB Glass-Covered Wire"; IEEE Trans. Magn. 33 (1997) 782.
H. Chiriac, et al.; "Amorphous Glass-Covered Magnetic Wires: Preparation, Properties, Applications"; Progress in Materials Science, 1996, 40, 333-407.
C.A. Grimes, et al.; Wireless Magnetoelastic Resonance Sensors: A Critical Review, Sensors 2, (2002) 294.

(Continued)

*Primary Examiner* — Maureen Wallenhorst
(74) *Attorney, Agent, or Firm* — Michael J. Renner, Esq.; Luedeka Neely Group, P.C.

(57) ABSTRACT

Disclosed is a sensor for detecting explosive devices. The sensor includes a ferromagnetic metal and a molecular recognition reagent coupled to the ferromagnetic metal. The molecular recognition reagent is operable to expand upon absorption of vapor from an explosive material such that the molecular recognition reagent changes a tensile stress upon the ferromagnetic metal. The explosive device is detected based on changes in the magnetic switching characteristics of the ferromagnetic metal caused by the tensile stress.

20 Claims, 4 Drawing Sheets

(56) References Cited

OTHER PUBLICATIONS

C.A. Grimes, et al.; "Magnetoelastic Sensors in Combination with Nanometer-scale Honeycombed Thin Film Ceramic TiO2 for Remote Query Measurement of Humidity"; Journal of Applied Physics, 87 (2000).

C.A. Grimes,e t al.; "Remote Query Pressure Measurement Using Magnetoelastic Sensors"; Rev. Sci. Instrum. 70 (1999) 4711.

M. Han, et al.; "Sensors Development Using Its Unusual Properties of Fe/Co-Based IAmorphous Soft Magnetic Wire"; J. Mater. Sci. 40 (2005) 5573.

J. Kravcak, et al.; "The Analysis of Large Barkhausen Effect in the FeSiB Amorphous Wire"; Cxech. J. Phys. 52 (2002) 175.

H. Lai, et al.; Identification of Volatile Chemical Signatures from Plastic Explosives by SPME-GC/MS and Detection by Ion Mobility Spectometry, Anal. Bioanal. Chem. 396 (2010) 2997.

K. Mohri, et al.; "Advances of Amorphous Wire Magnetic over 27 Years"; Phys. Status Solidi A, 206, pp. 601-607, Feb. 2, 2009.

D.S. Moore; "Recent Advances in Trace Explosives Detection Instrumentation"; Sens. Imaging 8 (2007) 9.

D.S. Moore; "Instrumentation for Trace Detection of High Explosives"; Rev. Sci. Instrum. 75 (2004) 2499.

M. Nambayah, et al.; "A Quantitative Assessment of Chemical Techniques for Detecting Traces of Explosives at Counter-Terrorist Portals"; Talanta 63 (2004) 461.

K.G. Ong, et al.; "Quantification of Multiple Bioagents With Wireless, Remote-Query Magnetoelastic Microsensors"; IEEE SEnsors Journal, vol. 6, No. 3, Jun. 2006.

K.G. Ong, et al.; "A Wireless, Passive, Magnetically-soft Harmonic Sensor for Monitoring Sodium Hypochlorite Concentrations in Water"; Sensors 2003, pp. 11-18.

J- M. Perr, et al.; "Solid Phase Microextraction Ion Mobility Spectrometer Interface for Explosive and Taggant Detection"; J. Sep. Sci. 28 (2005) 177.

L.P. P Shen, et al.; "Sensitive Stress-Impadence Micro Sensor Using Amorphous Magnetostrictive Wire"; IEEE Trans. Magn. 33 (1977) 3355.

J.I. Steinfeld, et al.; "Explosives Detection: A Challenge for Physical Chemistry", Annu. Rev. Phys. Chem. 49 (1998) 203.

M. Vazquez; "Soft Magnetic Wires"; Physica B 299 (2001)302.

M. Vazquez, et al.; "Magnetic Properties of Glass-Coated Amorphous and Nanocrystalline Microwires"; J. Magn. Magn. Mater. 160 (1996) 223.

A. Zhukov, et al.; "Microwires Coated by Glass: A New Family of Soft and Hard Magnetic Materials"; J. Mater. Res. 15 (2000) 2107.

* cited by examiner

WIRELESS SENSOR FOR DETECTING EXPLOSIVE MATERIAL

GOVERNMENT RIGHTS

The U.S. Government has rights to this invention pursuant to contract number DE-AC05-00OR22800 between the U.S. Department of Energy and Babcock & Wilcox Technical Services Y-12, LLC.

FIELD

This disclosure relates to the field of sensors for detecting explosives. More particularly, this disclosure relates to a highly sensitive and selective portable sensing device for detecting explosives.

BACKGROUND

Many common explosives, including materials used by modern terrorists, are very difficult to detect as they have very low vapor pressures at room temperature. When explosives are composited with organic materials to form plastic-bonded explosives (PBX), or are buried or concealed within parcels or clothing, the vapor pressures become vanishingly small. To achieve reliable detection through vapor-based methods, great volumes of air must be sampled. In addition, standard vapor pressure enhancing techniques such as heating may not be available as many explosives decompose at elevated temperatures. While a broad variety of approaches to detecting such explosives have been tried such as a trained dog, spectroscopy, separation followed by ion detection, immunochemical and electrochemical methods, and biosensors, no single technique concurrently satisfies the basic requirements of detection speed, selectivity, sensitivity, portability, affordability, and easy operability at a distance. What is needed therefore is an inexpensive explosives sensor that is sensitive to a broad range of explosives, can detect explosive materials rapidly, includes a sensing element that is capable of being interrogated wirelessly, and which can be embeddable in unobtrusive objects.

SUMMARY

According to one embodiment of the disclosure, a sensor for detecting explosive material is disclosed including a housing, a ferromagnetic metal disposed in the housing, and a molecular recognition reagent coupled to the ferromagnetic metal. The molecular recognition reagent is operable to expand upon absorption of vapor from the explosive material such that the molecular recognition reagent changes a tensile stress upon the ferromagnetic metal.

According to certain embodiments, the ferromagnetic metal is an amorphous wire preferably composed of a cobalt and iron based alloy. In an alternate embodiment, the ferromagnetic metal is an iron based alloy. In certain embodiments, the molecular recognition reagent is selected from the group consisting of methyl cellulose, polyethyleneimine, polyethylene oxide, polypropylene, polystyrene, polydimethylsiloxane, and Kraton® polymers.

In some embodiments, the ferromagnetic metal is mounted on opposing ends of the molecular recognition reagent and/or is at least partially coated with the molecular recognition reagent. In other embodiments, the molecular recognition reagent is attached to a fixed support disposed within the sensor wherein the molecular recognition reagent changes the tensile stress upon the ferromagnetic metal as the molecular recognition reagent expands away from the fixed support.

According to certain embodiments, the sensor further includes a detection mechanism having an inducing mechanism to induce alternating magnetic domains in the ferromagnetic metal and a detection mechanism to detect changes in magnetic switching characteristics of the ferromagnetic metal caused by the inducing mechanism and changes in the tensile stress of the ferromagnetic metal caused by absorption of the vapor from the explosive material by the molecular recognition reagent. In some embodiments, the inducing mechanism includes at least one drive coil and the detection mechanism includes at least one pickup coil and at least one cancellation coil.

According to another embodiment of the disclosure, a sensor for detecting an explosive device having explosive material includes a housing, a first sensing element disposed in the housing, and a second sensing element disposed in the housing. The first sensing element includes a first ferromagnetic metal and a first molecular recognition reagent coupled to the first ferromagnetic metal. The first molecular recognition reagent is operable to expand upon absorption of vapor from the explosive material such that the first molecular recognition reagent changes a first tensile stress upon the first ferromagnetic metal. The second sensing element includes a second ferromagnetic metal and a second molecular recognition reagent coupled to the second ferromagnetic metal. The second molecular recognition reagent is operable to expand upon absorption of the vapor from the explosive material such that the molecular recognition reagent changes a second tensile stress upon the second ferromagnetic metal. The second molecular recognition reagent is composed of a different composition than the first molecular recognition reagent such that the second sensing element responds differently than the first sensing element to the explosive material for assisting in identifying the explosive device.

According to certain embodiments, the ferromagnetic metal is an amorphous wire preferably composed of a cobalt and iron based alloy. In some embodiments, the first and second molecular recognition reagents are selected from the group consisting of methyl cellulose, polyethyleneimine, polyethylene oxide, polypropylene, polystyrene, polydimethylsiloxane, and Kraton® polymers.

In some embodiments, the sensor further includes a detection mechanism having an inducing mechanism to induce alternating magnetic domains in the first and second ferromagnetic metals and a detection mechanism to detect changes in magnetic switching characteristics of the first and second ferromagnetic metals caused by the inducing mechanism and changes in the tensile stress of the first and second ferromagnetic metals caused by absorption of the vapor from the explosive material by the first and second molecular recognition reagents.

According to yet another embodiment of the disclosure, a method of detecting an explosive device includes the steps of providing a sensor element including a ferromagnetic metal and a molecular recognition reagent coupled to the ferromagnetic metal; placing the sensor element in proximity to the explosive device such that the molecular recognition reagent expands upon absorption of vapor from an explosive material and the molecular recognition reagent changes a tensile stress upon the ferromagnetic metal; and detecting a change in the magnetic switching characteristics of the ferromagnetic metal resulting from the tensile stress imparted by the expansion of the molecular recognition reagent.

According to certain embodiments, the sensor element includes a plurality of ferromagnetic metal wires each having a different molecular recognition reagent coupled to the wire such that each metal wire responds differently to each explosive material of the explosive device. The method further includes selecting each molecular recognition agent from the group consisting of methyl cellulose, polyethyleneimine, polyethylene oxide, polypropylene, polystyrene, polydimethylsiloxane, and Kraton® polymers based on an affinity of the molecular recognition reagent to a particular explosive material.

BRIEF DESCRIPTION OF THE DRAWINGS

Various advantages are apparent by reference to the detailed description in conjunction with the figures, wherein elements are not to scale so as to more clearly show the details, wherein like reference numbers indicate like elements throughout the several views, and wherein.

DETAILED DESCRIPTION

In the following detailed description of the preferred and other embodiments, reference is made to the accompanying drawings, which form a part hereof, and within which are shown by way of illustration the practice of specific embodiments of explosives sensors. It is to be understood that other embodiments may be utilized, and that structural changes may be made and processes may vary in other embodiments. Further, it should be understood that this technology may be used in small, low-cost chemical sensors that have applications beyond explosives detection such as detecting chemical and biological warfare agents, volatile organic compounds, waste stream contents, air pollutants, food-borne pathogens, exhaled gases for health diagnostics or drug detection, etc.

Figure 1:
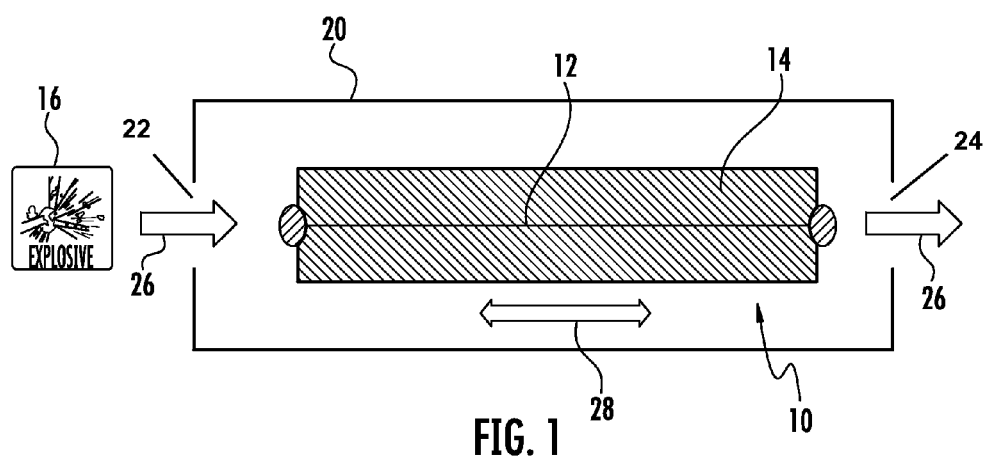
FIGS. 1 and 2 depict different embodiments of a sensing element having a magnetic wire coupled with a molecular recognition reagent according to the disclosure.

Referring to FIG. 1, the explosives sensor of the present disclosure includes a sensing element 10 that employs a ferromagnetic metal 12 coupled to a porous or perforated molecular recognition reagent 14. As shown in FIG. 1, the ferromagnetic metal is preferably configured as a mounted wire 12 and the molecular recognition reagent 14 is disposed around the wire. Alternatively, the molecular recognition reagent 14 could be coated onto the wire. A ribbon construction for the ferromagnetic metal may also be utilized within the spirit of the present disclosure. For purposes of illustration, the thickness of the molecular recognition reagent 14 in FIG. 1 has been greatly exaggerated with respect to the magnetic wire 12. In typical embodiments, the wire 12 will be about 25 to 40 microns in diameter and the molecular recognition reagent 14 will be about a micron or less in thickness.

In operation, the sensing element 10 is placed in proximity to an explosive device 16 such that vapor from the explosive material from the device 16 flows past the sensing element 10. As shown in the embodiment of FIG. 1, the sensing element 10 is disposed in a flow housing 20 having a first opening 22 and a second opening 24 such that the explosive material of explosive device 16 flows through the housing 20 and past the sensing element 10 as indicated by arrows 26. The molecular recognition reagent 14 is characterized by its affinity for gaseous components of particular explosive materials or taggants, and its ability to exhibit a large volume change per unit of explosive material absorbed. Thus, when detecting the explosive device 16, the molecular recognition reagent 14 expands which imposes stress on the magnetic wire 12 in both directions indicated by arrow 28. The sensing element 10 exploits the fact that, when subjected to alternating magnetic fields, the magnetic field strength and switching speed of the magnetic wire 12 varies as a function of tensile stress in the ferromagnetic wire 12 caused by the volume change of the molecular recognition reagent 14.

In preferred embodiments, the sensing element 10 will employ an array of ferromagnetic wires 12 coupled to a diverse set of molecular recognition reagents 14 such that each wire 12 will respond differently to each type of explosive material absorbed by the molecular recognition reagents 14. A neural network or other type of artificial intelligence based tool may then be employed to analyze and interpret the changes in the magnetic properties of the wires 12 to identify the presence of an explosive device or particular explosive materials. In other words, while every wire 12 and molecular recognition reagent 14 combinations in the array might react with every target material, the sensor employs computer learning algorithms that will detect different responses of all the wire/reagent combinations and will continually improve as new data regarding the detection of various materials becomes available. As each wire 12 responds differently to each explosive material, an effective "fingerprint" for each material is generated and the artificial intelligence tool is utilized to interpret the fingerprint and identify the explosive device.

In preferred embodiments, the magnetic wire 12 is an amorphous wire constructed from a ferromagnetic alloy having one or more glass forming components. The amorphous wire is preferably a Cobalt (Co) and Iron (Fe) based alloy such as $Co_{80.9}Fe_{4.4}Nb_{4.5}Si_{8.7}B_{1.5}$ with a diameter of about 25 to 40 microns. In alternate embodiment, the wire 12 is an iron based alloy (i.e., predominantly composed of iron). However, the particular combination of components and dimensions of the wire can be tailored for specific applications and an array of sensing elements 10 may include wires of varying alloys and/or diameters including diameters from about 5 to 125 microns. The amorphous characteristic of the wire 12 is produced during the alloy casting operation by rapid cooling from the molten to solid state. As a result, the material has a disordered atomic-scale (noncrystalline) structure. This noncrystalline structure leads to a higher tensile strength than that of material with an orderly structure. Further, the amorphous wire 12 has high magnetic susceptibility with low coercivity and high electrical resistance. Thus, the magnetic domains of the wires 12 can be switched when subjected to very small alternating magnetic fields. In addition, the amorphous wire magnetic domain switching properties are sensitive to stress. These properties of the amorphous magnetic wire 12 enable the sensing applications of the disclosed explosive sensors as further described below.

The molecular recognition reagents 14 are chosen from reactive materials that are operable to expand upon absorption of vapor from explosive materials. The space from which the molecular recognition reagents are chosen is large, and the choice depends on the particular target (e.g., explosive, chemical or biological warfare agent, pharmaceutical, etc.) that the sensor is intended to detect and the environment conditions in which the device is to be used. Such molecular recognition reagents include, but are not limited to, solid-phase microextraction (SPME) materials, metal-organic frameworks (MOFs), immobilized antibodies, classical zeolites, and other porous polymers and metals. Specific examples of molecular recognition reagents include, without limitation, the following: methyl cellulose, polyethyleneimine (PEI), polyethylene oxide (PEO), polypropylene (PP), polystyrene (PS), polydimethylsiloxane (PDMS), and Kraton® polymers (a synthetic replacement for rubber). As mentioned above, the sensing element 10 will preferably employ a diverse set of molecular recognition reagents 14 such that each wire 12 will respond differently to each type of explosive material absorbed by the molecular recognition reagents 14. Further, the particular configuration of the molecular recognition reagents 14 may vary based on the particular explosive material intended to be detected. For example, in embodiments where the explosive sensor is intended to detect large molecules such as provided in anthrax, the molecular recognition reagent may include an imprintable polymer having a "lock and key" arrangement for targeting the anthrax molecules. In other words, in the "lock and key" arrangement, the reagent surface includes specific geometric shapes complementary to the shapes of targeted particles.

Figure 2:
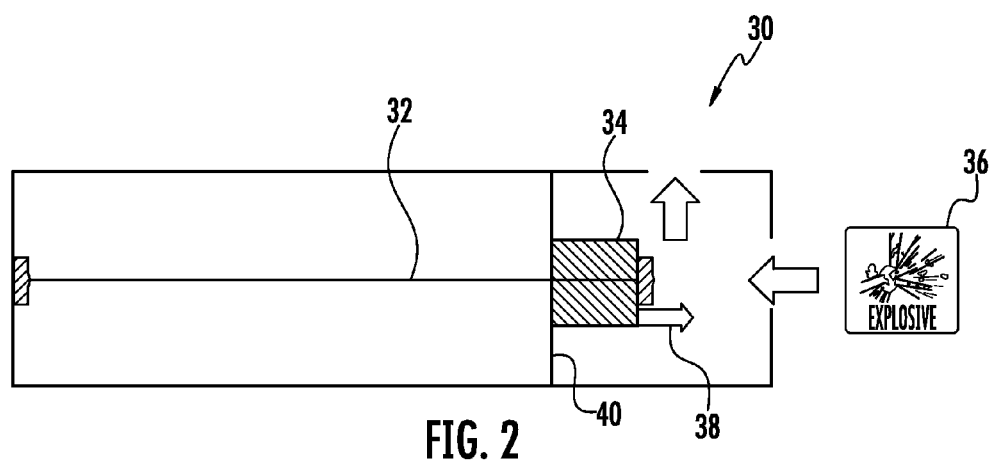

Referring to FIG. 2, an alternate embodiment of a sensing element 30 is shown in which the molecular recognition reagent 34 is secured to both the ferromagnetic wire 32 and a fixed support 40. When detecting an explosive device 36, the molecular recognition reagent 34 expands away from the fixed support 40 which imposes stress on the magnetic wire 32 in one direction as indicated by arrow 38.

In operation, a sensing element substantially as described above is placed in proximity to a potential explosive device such that the molecular recognition reagent of the sensing element expands upon absorption of vapor from an explosive material while an inducing mechanism is used to induce alternating magnetic domains in the ferromagnetic wire of the sensor. The expansion of the molecular recognition reagent changes a tensile stress upon the ferromagnetic wire, and a detection mechanism is used to detect changes in the switching properties of the ferromagnetic wire as a function of changes in the tensile stress of the wire.

Figure 3:
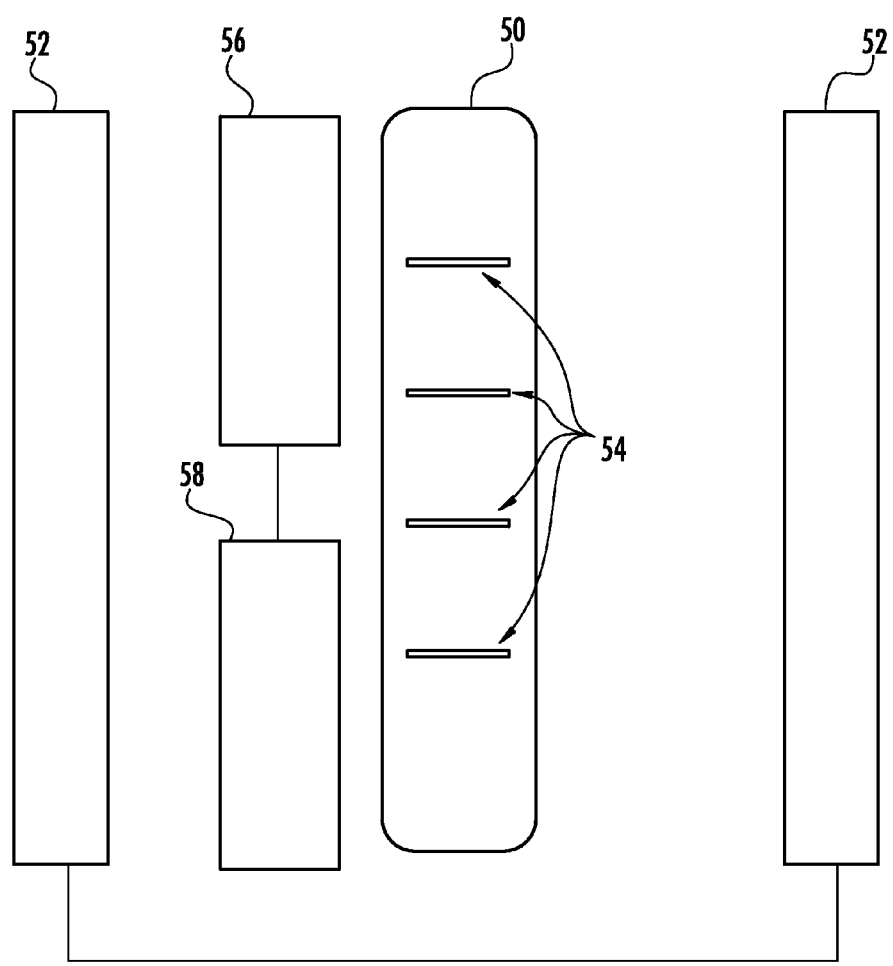
FIG. 3 depicts a schematic illustration of a sensing element detection mechanism according to the present disclosure.

FIG. 3 schematically illustrates a sensor 50 according to the present disclosure where one or more sensing elements 54 are detected by a detection mechanism composed of a system of at least one drive coil 52 and at least one pickup coil 56. Sensor 50 includes the sensing elements 54 positioned such that changes in the magnetic switching characteristics of the sensing elements 54 caused by drive coil 52 is detected by one or more pickup coils 56. An alternating current in the drive coil 52 creates the magnetic field which continually reverses the magnetic domains in the amorphous wire of the sensing elements 54. Reversal of the magnetic domains is detected with the pickup coil 52 as a peak which changes height based on tensile stress applied to the ferromagnetic wires by the molecular recognition reagents. In certain embodiments, one or more cancellation coils 58 may also be provided that are wired in an opposite direction from pickup coil 56. Cancellation coil 58 detects a similar drive coil magnetic field but does not detect a significant amount of the signal produced by switching of the ferromagnetic wire of sensing elements 54. The purpose of the cancellation coil is to cancel most of the magnetic field produced by the drive coils and eddy currents caused by the drive fields in conducting objects near the pickup coils 56.

Sensing element 54, drive coil 52, pickup coil 56, and cancellation coil 58 (if used) may be housed within a single unit sensor having a power source and wired or wireless communication means for transmitting data acquired from the sensing element 54, or the drive coil 52, pickup coil 56, and cancellation coil 58 (if used) may be provided in a separate unit from the sensing element 54.

Benefits of an explosives sensor such as those described above include the fact that the sensing element does not require radioactive sources and, in embodiments where the drive 52 and pickup coils 56 are provided in a separate unit from the sensing element 54, the sensing element does not require any type of physical power source or data transfer connection. Further one pickup coil is capable of detecting multiple sensing elements having various molecular recognition reagents without tedious alignment of the sensing elements. Thus, the sensor is small, inexpensive, and portable while offering the benefits of rapid detection while being highly selective and sensitive.

Figure 4A:
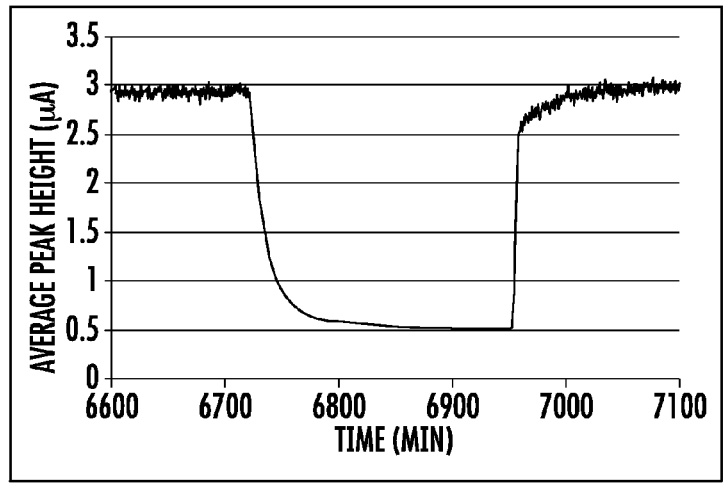
FIGS. 4A-4C depict peak height detection graphs for detecting methanol using a variety of molecular recognition reagents according to the disclosure.
Figure 4B:
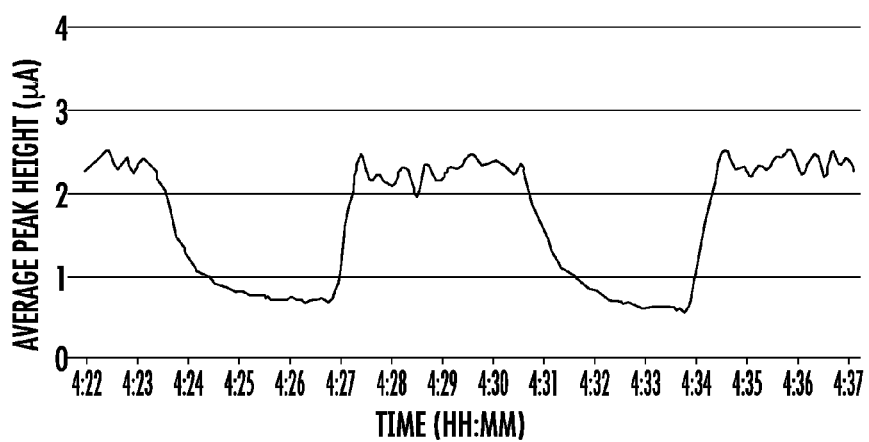
Figure 4C:
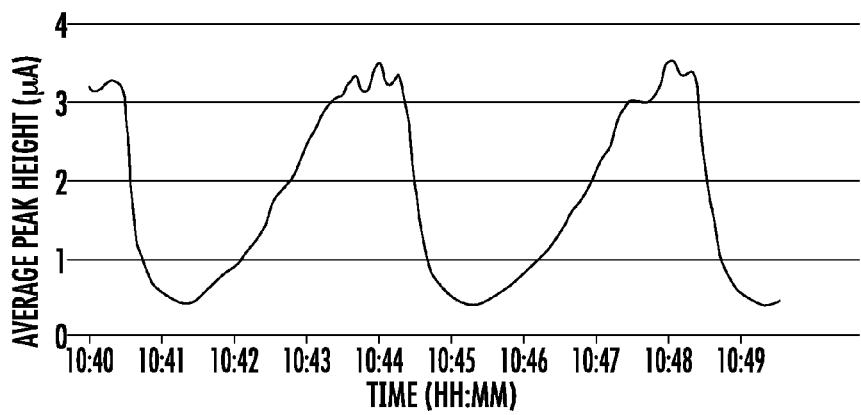

Referring to FIGS. 4A-4C, detection of methanol vapor entrained in a stream of air is shown when using a sensing element having various molecular recognition reagents. Referring to FIG. 4A, the molecular recognition reagent is methyl cellulose. Referring to FIG. 4B, the response to methanol of sensing element having a molecular recognition reagent composed of 100% polyethylene oxide (PEO) is provided, whereas FIG. 4C provides the response to methanol where the molecular recognition reagent is composed of 40% α-cyclodextrin and 60% PEO. It is also noted that a sensing element having 100% α-cyclodextrin as the molecular recognition reagent does not substantially respond to methanol (i.e., does not create tension in the amorphous wire). The heights of the peaks in the figures are dependent on the speed at which the amorphous wire domains reverse and the strength of the field produced by the wire. As tension is applied to the wire upon absorption of the methanol vapor by the particular molecular recognition reagent, the permeability of the amorphous wire decreases and the domain switching slows. Additionally, the amplitude of the field produced by the wire may decrease. This causes the peak current in the pick-up coil 56 of FIG. 3 to decrease with the increase in tension which is proportional to the amount and type of explosive material absorbed by the molecular recognition reagent. Slopes and shapes of the falling and rising signals, delay times, and peak heights detected by the pick-up coil may all be useful in determining the identity and concentration of a target and establishing a "fingerprint" for various explosive materials.

The foregoing descriptions of embodiments have been presented for purposes of illustration and exposition. They are not intended to be exhaustive or to limit the embodiments to the precise forms disclosed. Obvious modifications or variations are possible in light of the above teachings. The embodiments are chosen and described in an effort to provide the best illustrations of principles and practical applications, and to thereby enable one of ordinary skill in the art to utilize the various embodiments as described and with various modifications as are suited to the particular use contemplated. All such modifications and variations are within the scope of the appended claims when interpreted in accordance with the breadth to which they are fairly, legally, and equitably entitled.

What is claimed is:

1. A sensor for detecting explosive material comprising:
   a housing;
   a ferromagnetic metal disposed in the housing; and
   a molecular recognition reagent coupled to the ferromagnetic metal, the molecular recognition reagent operable to expand upon absorption of vapor from the explosive material such that the molecular recognition reagent changes a tensile stress upon the ferromagnetic metal.

2. The sensor of claim 1 wherein the ferromagnetic metal is an amorphous wire.

3. The sensor of claim 2 wherein the amorphous wire is composed of a cobalt and iron based alloy.

4. The sensor of claim 2 wherein the amorphous wire is composed of an iron based alloy.

5. The sensor of claim 1 wherein the ferromagnetic metal is mounted on opposing ends of the molecular recognition reagent.

6. The sensor of claim 1 wherein the ferromagnetic metal is at least partially coated with the molecular recognition reagent.

7. The sensor of claim 1 wherein the molecular recognition reagent is attached to a fixed support disposed within the sensor and wherein the molecular recognition reagent changes the tensile stress upon the ferromagnetic metal as the molecular recognition reagent expands away from the fixed support.

8. The sensor of claim 1 further comprising a detection mechanism, the detection mechanism including:
   an inducing mechanism to induce alternating magnetic domains in the ferromagnetic metal; and
   a detection mechanism to detect changes in magnetic switching characteristics of the ferromagnetic metal caused by the inducing mechanism and changes in the tensile stress of the ferromagnetic metal caused by absorption of the vapor from the explosive material by the molecular recognition reagent.

9. The sensor of claim 8 wherein the inducing mechanism includes at least one drive coil and the detection mechanism includes at least one pickup coil and at least one cancellation coil.

10. The sensor of claim 1 wherein the molecular recognition reagent is selected from the group consisting of methyl cellulose, polyethyleneimine, polyethylene oxide, polypropylene, polystyrene, polydimethylsiloxane, and polymers that serve as synthetic replacements for rubber.

11. A sensor for detecting an explosive device having explosive material, the sensor comprising:
   a housing;
   a first sensing element disposed in the housing including:
      a first ferromagnetic metal; and
      a first molecular recognition reagent coupled to the first ferromagnetic metal, the first molecular recognition reagent operable to expand upon absorption of vapor from the explosive material such that the first molecular recognition reagent changes a first tensile stress upon the first ferromagnetic metal; and
   a second sensing element disposed in the housing including:
      a second ferromagnetic metal; and
      a second molecular recognition reagent coupled to the second ferromagnetic metal, the second molecular recognition reagent operable to expand upon absorption of the vapor from the explosive material such that the second molecular recognition reagent changes a second tensile stress upon the second ferromagnetic metal,
   wherein the second molecular recognition reagent is composed of a different composition than the first molecular recognition reagent such that the second sensing element responds differently than the first sensing element to the explosive material for assisting in identifying the explosive device.

12. The sensor of claim 11 wherein the first and second ferromagnetic metal is an amorphous wire.

13. The sensor of claim 12 wherein the amorphous wire is composed of a cobalt and iron based alloy.

14. The sensor of claim 11 further comprising a detection mechanism, the detection mechanism including:
   an inducing mechanism to induce alternating magnetic domains in the first and second ferromagnetic metals; and
   a detection mechanism to detect changes in magnetic switching characteristics of the first and second ferromagnetic metals caused by the inducing mechanism and changes in the tensile stress of the first and second ferromagnetic metals caused by absorption of the vapor from the explosive material by the first and second molecular recognition reagents.

15. The sensor of claim 11 wherein the first and second molecular recognition reagents are selected from the group consisting of methyl cellulose, polyethyleneimine, polyethylene oxide, polypropylene, polystyrene, polydimethylsiloxane, and polymers that serve as synthetic replacements for rubber.

16. A method of detecting an explosive device comprising:
   providing a sensor element including a ferromagnetic metal and a molecular recognition reagent coupled to the ferromagnetic metal;
   placing the sensor element in proximity to the explosive device such that the molecular recognition reagent expands upon absorption of vapor from an explosive material and the molecular recognition reagent changes a tensile stress upon the ferromagnetic metal; and
   detecting a change in magnetic switching characteristics of the ferromagnetic metal resulting from the tensile stress imparted by the expansion of the molecular recognition reagent.

17. The method of claim 16 wherein the ferromagnetic metal is an amorphous wire.

18. The method of claim 17 wherein the amorphous wire is composed of a cobalt and iron based alloy.

19. The method of claim 16 wherein the sensor element includes a plurality of ferromagnetic metal wires each having a different molecular recognition reagent coupled to the wire such that each metal wire responds differently to each explosive material of the explosive device.

20. The method of claim 19 further comprising selecting each molecular recognition agent from the group consisting of methyl cellulose, polyethyleneimine, polyethylene oxide, polypropylene, polystyrene, polydimethylsiloxane, and polymers that serve as synthetic replacements for rubber based on an affinity of the molecular recognition reagent to a particular explosive material.

* * * * *